United States Patent [19]

Marconi et al.

[11] 4,252,645

[45] Feb. 24, 1981

[54] BIOCOMPATIBLE CELLULOSE TRIACETATE FIBRES FOR THE PURIFICATION OF BLOOD

[75] Inventors: Walter Marconi, San Donato Milanese; Romano Di Trapani, Monterotondo, both of Italy

[73] Assignee: Snamprogetti S.p.A., Milan, Italy

[21] Appl. No.: 816

[22] Filed: Jan. 4, 1979

[30] Foreign Application Priority Data

Jan. 26, 1978 [IT] Italy .................. 19623 A/78

[51] Int. Cl.³ .................. C02F 1/42; C08L 1/12; B01D 43/00
[52] U.S. Cl. .................. 210/688; 210/927; 260/17 R; 424/79
[58] Field of Search .................. 260/17 R; 210/38 R, 210/38 B

[56] References Cited

U.S. PATENT DOCUMENTS

| | | | |
|---|---|---|---|
| 1,885,475 | 11/1932 | Persiel | 106/170 |
| 2,955,017 | 10/1960 | Boyer | 264/184 |
| 3,408,291 | 10/1968 | Thomas et al. | 210/38 B |
| 3,885,069 | 5/1975 | Roberts et al. | 210/38 B |
| 3,957,698 | 5/1976 | Hatch | 210/38 R |

*Primary Examiner*—Edward M. Woodberry
*Attorney, Agent, or Firm*—Morgan, Finnegan, Pine, Foley & Lee

[57] ABSTRACT

A composition for the purification of blood in which impurities of the mercaptan class are present is disclosed, such composition being occluded in fibrous materials and consisting of a polymer functionalized with an organic mercury compound or with an anhydride of an organic acid. As the functionalizing compounds parachloromercury aniline, parachloromercurybenzoic acid and maleic anhydride are preferred.

6 Claims, No Drawings

BIOCOMPATIBLE CELLULOSE TRIACETATE FIBRES FOR THE PURIFICATION OF BLOOD

This invention relates to a novel composition for the purification of blood from impurities composed by mercaptans having a low molecular weight and refers also to the preparation of said composition as well to the uses thereof.

It is known that, during liver coma, there are formed in the human system a number of metabolites which are the principal cause of the persistance of the coma state. Among these, there are aromatic amino acids, fatty acids and mercaptans of low molecular weight. The present invention is just directed to solving the problem relating to these latter mercaptans by suggesting a method for synthesizing macromolecules, which, when occluded in non-thrombogeneric fibrous structures make up, with those fibres, the composition in question which is endowed with the property of suquestering, in the blood of patients having an acute hepatic insufficiency, low molecular weight mercaptans.

More detailedly, the composition the subject of the present invention is composed by functionalized water-soluble polymers occluded in bio-compatible fibers: examples of polymers suitable for this purpose are poly-acrylic acids and their anhydrides, the ethylene-maleic anhydride copolymers and all the kinds of soluble polysaccharides, either aminated, or carboxylated or unmodified. As functionalizing agents, there can be mentioned, for example, the organic-mercury compounds such as p.chloromercuroaniline and p.chloromer-curibenzoic acid. Still more, anhydrides of organic acids can be employed, such as maleic anhydride.

Now, the considerable reactivity is known of the mercury compounds for sulphydryl groups and this accounts for the considerable capability of attack these compounds have towards proteins. Thus, the sulphydryl group of small molecules, such as cysteine, has a great affinity for the mercury compounds: the reaction is reversible and the dissociation constant is $10^{-27}$ (Rothstein A., Mercury, Mercurials Mercaptans, Porc. Publ. Rochester Int. Conf. Environ Toxic 4th 1971 (Pub. 1973), (68–95), the pH and the presence of anions having a considerable influence of such reaction.

We have now found that it is possible to exploit the feature referred to above so as to functionalize water-soluble polymer in order to obtain compounds having an appropriate molecular weight which can be occluded in fibres and are capable of selectively capturing metabolites from biological fluids diffused through the interior of a fibre. In addition to the mercurial functionalization, a similar effect can be also obtained by previously reacting the polymer with maleic anhydride. By so doing, compositions can be obtained, which are bio-compatible as outlined above and which can be prepared in the form cartridges (these also having been made bio-compatible) which are then inserted in the extracorporal circulation path for the time which is required to capture the metabolites to be removed, in the case in point low molecular weight mercaptans.

The Assignee Company is the owner of two patent applications which relate, respectively, to the occlusion of sequestering agents in filamentary structures, and to a method for rendering materials of biologic interest biocompatible.

The first application, U.S. patent application Ser. No. 692,773 of June 4, 1976 is indicative of the possibility of occluding sequesting agents in filamentary structures through a number of stages, among which the dissolution or dispersion of the substance to be occluded in water, or mixture of water and glycerol deserve to be mentioned, together with the addition of the resultant admixture to a polymer solution and the spinning of the emulsion thus obtained.

The second application, U.S. Patent application Ser. No. 885,195 of Mar. 10, 1978 discloses the possibility of rendering polymeric materials biocompatible, fibres among the others, which is embodied either by occluding biocompatible agents in the materials of interest and in the case of fibres this addition can be made prior to spinning, or by coating the material concerned with the appropriate agents.

This invention has provided, on the basis of the teachings of the two applications mentioned above, to which reference is invited for the working details, a quite surprising combination which is such as to permit to have a composition according to what had been disclosed in the former application but which has the property of biocompatibility of the compositions according to the latter application. The fact was unpredictable on account of the nature of the occluded products, for which it was not possible to forecast that the behaviour in the free state towards the sulphydryl groups could be maintained unaffected also after the treatments briefly recalled hereinabove.

For each and every detail, reference is invited to the ensuing working example by which the invention is intended to be illustrated without limiting the scope thereof, since anyone skilled in the art will be in a position, once the principle of the invention has been appraised, to vary the nature of the several components and thus to prepare a number of compositions adapted to purify the blood in the sense indicated hereinabove.

EXAMPLE 1

0.5 grams of p-acetoxymercuryaniline (K & K Laboratories, Inc. Plainview, N.Y.) has been dissolved in 20 mls of dimethylformamide and then added with stirring and at the temperature of 0° C. to a solution of 1 gram of ethylene-maleic anhydride copolymer (Polysciences Inc., Warrington, USA) in dimethylformamide (50 mls). After stirring overnight, the mixture has been diluted with 100 mls of water which contained 0.5 gram of NaCl to convert the p.acetoxymercuryaniline bound to the polymer into its chlorinated form. Upon 24-hour dialysis against deionized water in a cellulose tube (Arthur H. Thomas Company, Philadelphia, USA), so as to exclude the compounds having molecular weights below 8,000, the product has been dried. A portion of the functionalized polymer (about 150 milligrams) has been dissolved in water and adjusted to a pH of 7.4 with conc. NaOH. The aqueous solution which has been obtained has been emulged with a solution of TAC (cellulose triacetate) in $CH_2Cl_2$ which contained 4,5-diphenyl-2-bis-(2 -hydroxyethyl) amino oxazole whereafter the fibre has been obtained with the procedure disclosed in U.S. Patent application Ser. No. 692,773 of June 4, 1976 already cited. After having washed for several days the fibre with isotonic solution, the test of absorption of nor.butyl mercaptan from a solution thereof in water at a concentration of about $1.10^{-3}$ M has been carried out. The result which has been obtained was that for each gram of dry fibre, saturation was achieved within about three hours, 90 micromols of nor.butylmercaptan having thus been absorbed. The determination of the -SH groups in solution has been carried out according to the procedure described by Roberts E., and Rouser G., (1958), Anal. Chem., 30 1292.

EXAMPLE 2

0.4 gram of p-acetoxymercuryaniline (K & K Laboratories, Inc., Plainview, N.Y.) has been dissolved in 20 mls of dimethylformamide and then added with stirring and at the temperature of 0° C. to a solution of 0.88 gram of polyacrylic anhydride (mol wt 150,000) in 50 mls of dimethylformamide. The procedure of Example 1 hereof has been then followed carefully and there were obtained 850 milligrams of a polymer, which have been occluded in a cellulose triacetate fibre which had been made biocompatible as outlined above. The total quantity of fibre which has been obtained was 10 grams approximately. After having washed the fibre repeatedly for several days, a kinetic absorption test of non-butylmercaptan has been carried out from an isotonic solution having a concentration of $1.10^{-3}$ M. The table reported below tabulates the trend of the absorption in micromols per gram of dry fibre:

| Micromols per gram of dry fibre: | | | | | | |
|---|---|---|---|---|---|---|
| Time, minutes | 10 | 30 | 90 | 250 | 330 | 360 |
| Micromols of nor.butymercaptan absorbed | 48 | 70 | 100 | 165 | 169 | 150 |

EXAMPLE 3

A fibre prepared exactly according to the procedure of Example 2 hereof has been tested for absorption of L-cysteine from an isotonic solution thereof of the concentration of $1.10^{-3}$ M approximately. The trend of the absorption as a function of time, in micromols per gram of dry fibre, is tabulated hereunder:

| Time, minutes | 10 | 30 | 90 | 250 | 330 | 360 |
|---|---|---|---|---|---|---|
| Micromols of L-cysteine absorbed | 52 | 88 | 145 | 182 | 185 | 185 |

EXAMPLE 4

A fibre prepared exactly according to the procedures of Examples 2 and 3 above, has been tested for absorption of glutathione (GSH) and of reduced glutathione (GSSG) from $1.10^{-3}$ isotonic solutions.

While in the former case absorption by the fibre has been experienced, in the latter case of the reduced glutathione, this fact did not occur.

For the analysis of the glutathione in solution the ninhydrin method has been adopted as disclosed by S. Moor and W. Stein, J. Biol. Chem., 176, 367 (1948). The trend of the absorption as a function of time in micromols per gram of dry fibre is tabulated hereunder:

| Time, minutes | 10 | 30 | 90 | 250 | 330 | 360 |
|---|---|---|---|---|---|---|
| Micromols of GSH, absorbed | 25 | 50 | 90 | 138 | 140 | 140 |

EXAMPLE 5

A fibre prepared according to the same procedures as in the foregoing examples 2, 3 and 4 has been absorption-tested for nor.butyl mercaptan in human blood serum, to which the mercaptan had been added in a concentration of $1.10^{-3}$ M. For the determination of nor. butylmercaptan, the procedure has been to extract the latter with ethyl ether and then gaschromatographic analysis has been carried out.

The trend of the absorption as a function of time, in micromols per gram of dry fibre is tabulated hereunder:

| Time, minutes | 10 | 30 | 90 | 250 | 330 | 360 |
|---|---|---|---|---|---|---|
| Micromols of nor.butylmercaptan, absorbed | 15 | 40 | 75 | 120 | 125 | 125 |

We claim:
1. A composition adapted to the purification of blood, composed of functionalized water soluble polymers occluded in biocompatible cellulose triacetate fibres.
2. Composition according to claim 1, wherein the polymer is a member selected from the group consisting of polyacrylic acids, their anhydrides, ethylene-maleic anhydride copolymer and the soluble polysaccharides.
3. Composition according to claim 1 or 2 wherein the functionalizing agent is a member selected from the group consisting of the organic mercurial compounds and the anhydrides of organic acids.
4. Composition according to claim 3, wherein the mercurial organic compound is a member selected from the group consisting of p-chloromercuryaniline and p-chloromercurybenzoic acid.
5. Composition according to claim 3, wherein the anhydride is maleic anhydride.
6. A method for purifying blood from metabolites consisting of a low molecular weight mercaptans, comprising the step of contacting the metabolite-polluted blood with a composition according to claim 1.

* * * * *